ns pages).

(12) United States Patent
Louis

(10) Patent No.: US 9,815,937 B2
(45) Date of Patent: *Nov. 14, 2017

(54) PROCESS FOR PREPARING A POLY(ARYL ETHER KETONE) USING A HIGH PURITY 4,4'-DIFLUOROBENZOPHENONE

(71) Applicant: Solvay Advanced Polymers, L.L.C., Alpharetta, GA (US)

(72) Inventor: Chantal Louis, Alpharetta, GA (US)

(73) Assignee: Solvay Advanced Polymers, L.L.C., Alpharetta, GA (US)

( * ) Notice: Subject to any disclaimer, the term of this patent is extended or adjusted under 35 U.S.C. 154(b) by 19 days.

This patent is subject to a terminal disclaimer.

(21) Appl. No.: 14/861,508

(22) Filed: Sep. 22, 2015

(65) Prior Publication Data

US 2016/0145386 A1 May 26, 2016

Related U.S. Application Data

(63) Continuation of application No. 13/125,523, filed as application No. PCT/EP2009/064008 on Oct. 23, 2009, now abandoned.

(60) Provisional application No. 61/140,205, filed on Dec. 23, 2008, provisional application No. 61/108,096, filed on Oct. 24, 2008, provisional application No. 61/108,097, filed on Oct. 24, 2008.

(51) Int. Cl.

| C08G 65/40 | (2006.01) |
|---|---|
| C07C 315/06 | (2006.01) |
| C08G 8/02 | (2006.01) |
| C01D 7/00 | (2006.01) |
| C07C 45/78 | (2006.01) |
| C08G 75/23 | (2006.01) |

(52) U.S. Cl.
CPC ........... *C08G 65/4012* (2013.01); *C01D 7/00* (2013.01); *C07C 45/78* (2013.01); *C07C 315/06* (2013.01); *C08G 8/02* (2013.01); *C08G 65/4087* (2013.01); *C08G 65/4093* (2013.01); *C08G 75/23* (2013.01); *C08G 2261/3444* (2013.01)

(58) Field of Classification Search
CPC .............................................. C08G 65/4012
See application file for complete search history.

(56) References Cited

U.S. PATENT DOCUMENTS

| 4,814,508 | A | 3/1989 | Gors et al. |
| 5,194,561 | A | 3/1993 | Fischer et al. |
| 5,777,172 | A | 7/1998 | Standen et al. |
| 6,828,353 | B1 | 12/2004 | Charnock et al. |
| 2005/0010015 | A1 | 1/2005 | Zhang et al. |
| 2007/0265415 | A1 | 11/2007 | Richter et al. |

FOREIGN PATENT DOCUMENTS

| EP | 001879 A1 | 5/1979 |
| EP | 275035 A2 | 7/1988 |
| EP | 0303389 A2 | 2/1989 |
| WO | 2005/030836 A1 | 4/2005 |
| WO | 2007/014692 A1 | 2/2007 |
| WO | 2007/144610 A1 | 12/2007 |
| WO | 2007/144615 A1 | 12/2007 |
| WO | 2009/021918 A1 | 2/2009 |
| WO | 2010/046482 A1 | 4/2010 |
| WO | 2010046484 A1 | 4/2010 |

OTHER PUBLICATIONS

Blundell et al., Polymer, 1983, vol. 24, 953-958.*
Decision Revoking the European Patent No. EPB2342259 issued in European Application No. 09740140; dated Nov. 8, 2016 (32 pages).
"Comprehensive Polymer Science", vol. 5, Chapter 29 (1988), p. 483-497 (10 pages).
"Synthesis, characterization and thermal degradation studies of poly(ether ether ketone) copolymers", Rao, M.R. et al., Polymer, vol. 33, No. 13 (1992), p. 2834-2839 (6 pages).
Evidence relating to Aldrich 4,4'Difluorobenzophenone (3 pages).
Prriority document U.S. Appl. No. 61/108,097, filed Oct. 24, 2008 (35 pages).
Prriority document U.S. Appl. No. 61/140,205, filed Dec. 23, 2008 (48 pages).
Prriority document U.S. Appl. No. 61/108,096, filed Oct. 24, 2008 (51 pages).
Certificate of Analysis; Vision Fluorochem (Nanjing) Ltd. (3 pages).
Certificate of Analysis; Changzhou Huashan CHemical Co., Ltd. (4 pages).
Supplementary Experimental data and analysis (1 page).
UK Catalogue of chemical reagents; Fisher Scientific (1 page).
"Crystallinity Increases in Semi Crystalline Polymers During High Rate Testing", Swallowe, G.M. et al., J. Phys IV France 7 (1997), p. C3-453-C3-458 (6 pages).
"Differential scanning calorimetry and infra-red crystallinity determinations of poly(aryl ether ketone)", Jonas, A. et al., Polymer, vol. 32, No. 18 (1991), p. 3364-3370 (7 pages).
"Miscible Blends of Poly(aryl Ether Ketone)s and Polyetherimides", Harris, J.E. et al, Journal of Applied Polymer Science, vol. 25 (1998), p. 1877-1891 (8 pages).
Experimental Evidence relating to commercial PEEK samples sold in 2005 (1 page).
Diphenyl Sulphone Data Sheet—Seal Sands Chemicals Ltd. (1994) (1 page).
Analysis of Sigma Aldrich DPS Lot 06204 TH publicly released Dec. 2007—and related evidence (6 pages).
Additional data submitted by the Patent Proprietor with the reply to the Summons to Oral Proceedings—EP 2342259 B1 (3 pages).

* cited by examiner

*Primary Examiner* — Liam J Heincer
(74) *Attorney, Agent, or Firm* — Osha Liang LLP

(57) ABSTRACT

The present invention describes a process for preparing a poly(aryl ether ketone) by reacting a nucleophile with 4,4'-difluorobenzophenone (4,4'-DFBP) that is improved through the use of 4,4'-DFBP that meets one or more particular purity conditions. Also described are improved poly(aryl ether ketone) produced using the invention 4,4'-DFBP. Amounts of 2,4'-difluorobenzophenone (2,4'-DFBP), 4-monofluorobenzophenone (4-FBP), chlorine, and monochloromonofluorobenzophenone in 4,4'-DFBP are discussed.

14 Claims, 1 Drawing Sheet

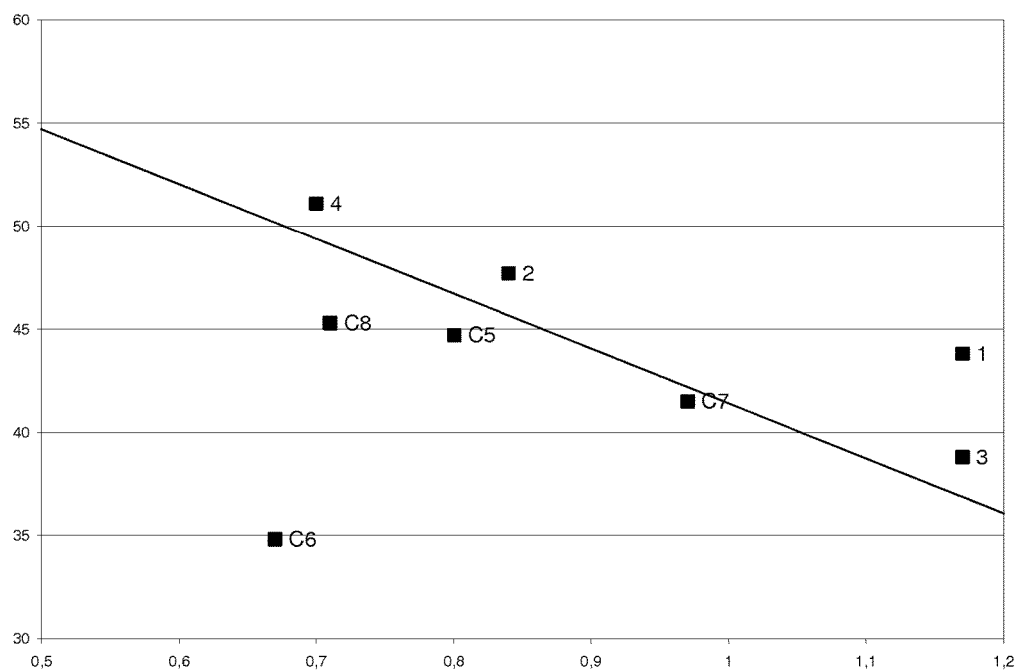

PROCESS FOR PREPARING A POLY(ARYL ETHER KETONE) USING A HIGH PURITY 4,4'-DIFLUOROBENZOPHENONE

CROSS REFERENCE TO RELATED APPLICATIONS

The present application is a continuation application of U.S. patent application Ser. No. 13/125,523, which is a national stage entry under 35 U.S.C. 371 of International Application No. PCT/EP2009/064008 filed Oct. 23, 2009, which claims the priority benefit to U.S. provisional application No. 61/108,096 filed on Oct. 24, 2008, to U.S. provisional application No. 61/108,097 filed on Oct. 24, 2008, and to U.S. provisional application No. 61/140,205 filed on Dec. 23, 2008, the whole content of all these applications being herein incorporated by reference for all purposes.

FIELD OF THE INVENTION

The present invention relates to highly pure 4,4'-difluorobenzophenone (4,4'-DFBP). Also described is the use of this highly pure 4,4'-DFBP in the preparation of poly(aryl ether ketone) polymers (PAEK), and the resulting PAEK polymers.

BACKGROUND OF THE INVENTION 4,4'-difluorobenzophenone (4,4'-DFBP) is a well known chemical intermediate having the following chemical formula:

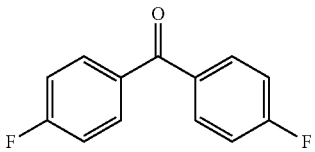 [SMILES: O=C(c1ccc(F)cc1)c1ccc(F)cc1]

4,4'-DFBP is known to be useful in the preparation of, e.g., PAEK polymers such as PEEK and PEK. PAEK polymers are a well known class of engineering polymers useful in various fields of endeavour. Processes for preparing PAEK polymers, including those using 4,4'-DFBP, can be found in, e.g., U.S. Pat. Nos. 3,953,400, 3,956,240, 3,928,295, and 4,176,222, all incorporated herein by reference. Generally, PAEK polymers are prepared by aromatic nucleophilic substitution. For example, p-hydroquinone, commonly referred to as "hydroquinone", a bisphenol, etc. can be used as a nucleophilic component which is deprotonated with a base such as NaOH, $Na_2CO_3$ or $K_2CO_3$ to form a nucleophile that then reacts with, e.g., a dihalobenzophenone such as 4,4'-DFBP to form a PAEK polymer via nucleophilic substitution, with the fluorine atoms of the 4,4'-DFBP acting as leaving groups.

It is generally known that purified starting materials are preferred in the chemical synthesis of complex molecules, and this is true for monomers used in the synthesis of PAEK polymers. For example, WO2007/144610 and WO2007/144615 describe the use of monomers having a purity of at least 99.7 area %, including 99.9 area % (as measured by gas chromatography), as providing improved melt flow index in the product polymer. It should be noted that a material that is 99.9% pure contains 1000 ppm of one or more impurities. However, these references remain silent on the nature and amount of specific impurities to be avoided. In addition, this measurement by area % leads only to a general purity level of the monomers and is nonspecific with regard to the type and amount of specific impurities to be avoided.

Common impurities of 4,4'-difluorobenzophenone are for example other positional isomers (mainly the 3, 4' and 2, 4' isomers), coloured impurities and polymeric by-products as described in U.S. Pat. No. 5,777,172.

Semi-crystalline poly(aryl ether ketone)s exhibit interesting properties as compared to their amorphous counterparts including, notably, excellent chemical resistance and good mechanical properties over a large temperature range. Ultimate mechanical properties of semi-crystalline resins are in particular linked to the crystallinity level. A high level of crystallinity is thus important to maintain these properties. Another important property of PAEK polymers is their melt stability.

There is a long felt need for PAEK polymer having improved chemical resistance and mechanical properties over a large temperature range, and therefore PAEK polymer with improved crystallinity and/or melt stability are needed.

SUMMARY OF THE INVENTION

The art, while generally recognizing that the purity of 4,4'-DFBP can have an influence on PAEK polymers obtained therewith, does not identify which impurities in 4,4'-DFBP should be limited, and to what extent. This is in particular true for semi-crystalline PAEK polymers, which have different monomer purity requirements from amorphous PAEK. Only semi-crystalline PAEK have gained wide acceptance due to their increased chemical resistance properties. A semi-crystalline polymer is a polymer which crystallizes on cooling from the melt or from solution. The amount of crystallinity can be determined by different methods ("Crystallinity Determination", J. Runt, M. Kanchanasopa, "Encyclopaedia Of Polymer Science and Technology", Online Ed, 2004), Wide Angle X-Ray diffraction (WAXD) or Differential Scanning calorimetry (DSC) are two common methods used to determine crystallinity. By DSC, the reference (Blundell et al., Polymer, 1983, V 24, P 953) is that a fully crystalline PEEK exhibits an enthalpy of fusion of 130 J/g. Semi-crystalline PAEK have crystallinity levels of above 5%, preferably above 10% as measured by WAXD or by DSC.

As will be explained in detail below, the present inventor has now discovered that when the amounts of specific impurities in 4,4'-DFBP, namely 2,4'-difluorobenzophenone, 4-monofluorobenzophenone and chlorinated organics, are controlled as described herein a PAEK polymer is obtained having improved crystallinity and/or melt stability. The inventor has also discovered that the presence of chlorine end groups has a deleterious effect on the stability of the whole polymer.

The method described in WO2007/144610 and WO2007/144615 does not allow baseline separation of the 2,4'-difluorobenzophenone and 4-monofluorobenzophenone impurities found in 4,4'-DFBP: hence a quantitative determination of these key impurities is ambiguous using this method. In fact, the quite similar structures and boiling points of the different difluorobenzophenone isomers lead to complicated chromatograms where the isomers cannot be clearly and unambiguously separated from each other (overlapping or shouldering), when using common high pressure liquid chromatography (HPLC) or gas chromatography (GC) methods.

The inventor of the present invention has found out that the gas chromatography method described in WO2007/144610 and WO2007/144615 is not suitable for the purity determination of DFBP, since it does not allow the differentiation of specific impurities. The inventor has found out that the liquid chromatography analysis of DFBP is much more appropriate and allows the detection of specific impurities which presence has an adverse effect on the PAEK properties.

BRIEF DESCRIPTION OF THE DRAWING

For a detailed description of the invention, reference will now be made to the accompanying drawing in which:

The FIGURE represents a graph of the enthalpy of fusion of polymers according to the present invention versus the reduced viscosity (RV) of the polymers.

DETAILED DESCRIPTION OF THE PREFERRED EMBODIMENTS

PAEK are generally prepared by aromatic nucleophilic substitution, i.e. a fundamental class of substitution reaction in which an "electron rich" nucleophile selectively bonds with or attacks the positive or partially positive charge of an atom attached to a group or atom called the leaving group; the positive or partially positive atom is referred to as an electrophile. A nucleophile is thus intended to denote a reagent that forms a chemical bond to its reaction partner (the electrophile) by donating both bonding electrons. Common nucleophilic monomers used in the synthesis of PAEK are hydroxylated monomers such as p-hydroquinone (commonly known as "hydroquinone"), 4,4'-dihydroxybenzophenone, 4,4'-biphenol, 1,4-bis-(p-hydroxybenzoyl)benzene, 1,3-bis-(p-hydroxybenzoyl)benzene, etc. On the other hand, common electrophilic monomers used in the synthesis of PAEK are 4,4'-difluorobenzophenone, 1,4-bis(p-fluorobenzoyl)benzene; 1,3-bis(p-fluorobenzoyl)benzene, 4,4'-bis(p-fluorobenzoyl)biphenyl, etc. 4,4'-DFBP is frequently used as an electrophile in the preparation of PAEK polymers such as PEEK and PEK. In studying 4,4'-DFBP impurities the inventor has found that 2,4'-difluorobenzophenone (2,4'-DFBP), 4-monofluorobenzophenone (4-FBP), and monochloromonofluorobenzophenone (chlorofluorobenzophenone, ClFBP) to be commonly present in commercially available 4,4'-DFBP. In addition, the inventor has discovered that both 2,4'-DFBP and 4-FBP have a deleterious effect on PAEK crystallinity as measured by the heat of fusion on the $2^{nd}$ heat cycle in DSC and that chlorofluorobenzophenone has a deleterious effect on PAEK resin melt stability.

The inventor, after much study, has further discovered that in order to maintain acceptable crystallinity the levels of 2,4'-DFBP and 4-FBP in 4,4'-DFBP should obey a particular relationship with regard to their amount present.

A first aspect of the present invention is thus related to a process for preparing a PAEK by reacting a nucleophile with 4,4'-difluorobenzophenone (4,4'-DFBP), the improvement comprising using a 4,4'-DFBP that meets at least one, and preferably both, of the following impurity limitations:
[2,4'-difluorobenzophenone]≤750 ppm,
[2,4'-difluorobenzophenone]+[4-monofluorobenzophenone]≤1250 ppm
wherein the amounts of 2,4'-difluorobenzophenone and 4-monofluorobenzophenone in 4,4'-difluorobenzophenone are determined by liquid chromatography analysis, as described in the following examples;

where these expressions mean that:
the content of 2,4'-DFBP in the 4,4'-DFBP is less than or equal to 750 ppm and
the content of 2,4'-DFBP in the 4,4'-DFBP plus the content of 4-FBP in the 4,4'-DFBP is in total less than or equal to 1250 ppm.

In the description, impurities levels are expressed on weight basis, i.e. weight of the impurity of concern/(weight of the 4,4'-DFBP+weight of all present impurities), expressed either in parts per million or in wt. %.

Generally chromatographic data is presented as a graph of detector response (y-axis) against retention time (x-axis). This provides a spectrum of peaks for a sample representing the analytes present in a sample eluting from the column at different times. Retention time can be used to identify analytes if the method conditions are constant. Also, the pattern of peaks will be constant for a sample under constant conditions and can identify complex mixtures of analytes. In most modern applications however the GC or LC apparatus is connected to a mass spectrometer or similar detector that is capable of identifying the analytes represented by the peaks. The area under a peak is proportional to the amount of analyte present. By calculating the area of the peak using the mathematical function of integration, the concentration of an analyte in the original sample can be determined. In most modern systems, computer software is used to draw and integrate peaks.

In the process according to the present invention the 4,4'-DFBP contains at most 750 ppm of 2,4'-difluorobenzophenone.

Preferably, the 4,4'-DFBP meets the following impurity limitations:
[2,4'-difluorobenzophenone]≤750 ppm, more preferably 300 ppm, and
[4-monofluorobenzophenone]≤950 ppm, more preferably 500 ppm.

In a preferred embodiment the 4,4'-DFBP meets the following impurity limitations: [2,4'-difluorobenzophenone]≤750 ppm, and [4-monofluorobenzophenone]≤500 ppm.

In another preferred embodiment the 4,4'-DFBP meets the following impurity limitations: [2,4'-difluorobenzophenone]≤300 ppm, and [4-monofluorobenzophenone]≤950 ppm.

In another preferred embodiment [2,4'-DFBP]≤750 ppm (including 700, 650, 600, 550, 500, 450, 400, 350, 300, 250, 200, 150, 100, 50 ppm etc., of course including 0 ppm, and all values and subranges between stated values as if explicitly written out) and [4-FBP]≤500 ppm (including ≤450, 400, 350, 300, 250, 200, 150, 100, 50 ppm etc., of course including 0 ppm, and all values and subranges between stated values as if written out).

In another preferred embodiment [2,4'-DFBP]≤300 ppm (including ≤250, 200, 150, 100, 50 ppm etc., of course including 0 ppm, and all values and subranges between stated values as if explicitly written out) and [4-FBP]≤950 ppm (including ≤900, 850, 800, 750, 700, 650, 600, 550, 500, 450, 400, 350, 300, 250, 200, 150, 100, 50 ppm etc., of course including 0 ppm, and all values and subranges between stated values as if explicitly written out).

In another preferred embodiment [2,4'-difluorobenzophenone]+[4-monofluorobenzophenone]≤1250 ppm (including ≤1200, 1100, 1000, 900, 800, 700, 600, 500, 400, 300, 200, 100, 50 ppm etc., of course including 0 ppm, and all values and subranges between stated values as if explicitly written out).

In another preferred embodiment the total chlorine content (representing the chlorinated organics) in the 4,4'-DFBP should be 0.075 wt % or less, preferably 0.053 wt % or less (including 0.05, 0.045, 0.040, 0.035, 0.030, 0.025, 0.020 wt % or less etc., of course including 0 wt %, and all values and subranges between stated values as if written out) which, expressed as chlorofluorobenzophenone, is ≤5000, ppm, 3500 ppm or less (including ≤3400, 3300, 3200, 3100, 3000, 2750, 2500, 2250, 2000, 1750, 1500, 1250, 1000, 900, 850, 800, 750, 700, 650, 600, 550, 500, 450, 400, 350, 300, 250, 200, 150, 100, 50 ppm etc., of course including 0 ppm, and all values and subranges between stated values as if explicitly written out. Chlorofluorobenzophenone contains 15% of the chlorine element; so 0.053% chlorine=530 ppm Cl= (530/0.15) ppm chlorofluorobenzophenone=3530 ppm.

This total chlorine content (representing the chlorinated organics) in the 4,4'-DFBP is determined by Total Organic Halogen analysis (TOX), i.e. by combustion followed by microcoulometric titration analysis (TOX), as described in the following examples.

In a particular embodiment, the 4,4'-difluorobenzophenone used in the process according to the present invention may have a GC purity of ≤99.9 area %, and even ≤99.9 area %, since some impurities have no adverse effect on the PAEK properties.

Another aspect of the present invention is related to a 4,4'-DFBP that meets all the above described impurity limitations, and in particular:
[2,4'-difluorobenzophenone]≤750 ppm and [2,4'-difluorobenzophenone]+[4-monofluorobenzophenone]≤1250 ppm.

Preferably, the 4,4'-DFBP according to the present invention meets the following impurity limitations:
[2,4'-difluorobenzophenone]≤750 ppm, more preferably 300 ppm and
[4-monofluorobenzophenone]≤950 ppm, more preferably 500 ppm.

In another preferred embodiment, the 4,4'-DFBP according to the present invention meets at least two, preferably at least three and more preferably all the above mentioned impurity limitations.

Still another aspect of the present invention is related to PAEK polymer obtainable by or prepared according to the process as above described.

Improved melt stability and/or improved crystallinity may be observed under these conditions. Ultimate mechanical properties of semi-crystalline resins are linked to the crystallinity level. The enthalpy of fusion as measured by DSC provides an easy measure of the polymer crystallinity level.

Acceptable crystallinity depends on the polymer (PEEK is different from PEK) and on the polymer molecular weight as measured by its reduced viscosity (RV). The inventor has found out that acceptable ranges, i.e. those leading to good mechanical properties, for PEEK and PEK are as follows. For PEEK, the acceptable enthalpy of fusion, also described as the target enthalpy of fusion, is ≥68.0-26.6*RV, (more preferably ≥69.0-26.6*RV) wherein RV is the reduced viscosity measured in $H_2SO_4$. For PEK it is ≥72.0-21.0*RV; more preferably ≥74.0-21.0*RV.

Another aspect of the present invention is thus related to a poly(aryl ether ketone), wherein the poly(aryl ether ketone) is PEEK having a heat of fusion in J/g≥68.0-26.6*RV (dl/g) where RV is the polymer reduced viscosity measured at 25° C. in concentrated $H_2SO_4$, or wherein the poly(aryl ether ketone) is PEK.

Melt stability can be measured by the ratio of melt flow index measured at different holding times. Details of the methods are described further. Melt flow ratio (MFR) is preferably between 0.5 and 1.5, preferably between 0.5 and 1.2.

Amounts of all these impurities (2,4'-DFBP, 4-FBP, total chlorine content, chlorofluorobenzophenone) can be measured in the 4,4'-DFBP using the test methods described in examples. Enthalpy of fusion can be determined by DSC as described in the examples. All of these measurement techniques are within the skill of the ordinary artisan.

It is within the skill of the ordinary artisan to purify 4,4'-DFBP in order to meet, both singly and collectively, the above impurity limits for all of 2,4'-DFBP, 4-FBP, total chlorine content, and chlorofluorobenzophenone using, for example, techniques such as chromatography, washing with a non solvent, dissolution in a solvent at high temperature and recrystallization at low temperature, distillation optionally under vacuum, ion exchange, etc.

4,4'-DFBP meeting one or more of the purity descriptions herein is particularly useful in the preparation of poly(aryl ether ketone) (PAEK) polymers.

The term "poly(aryl ether ketone)" (PAEK) as used herein includes any polymer of which more than 50 wt. % of the recurring units are recurring units (R1) of one or more formulae containing at least one arylene group, at least one ether group (—O—) and at least one ketone group [—C(=O)—] and which was prepared using 4,4'-DFBP as a starting material.

Preferably, recurring units (R1) are chosen from:

(I)

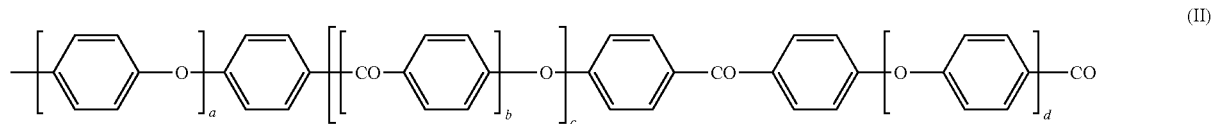

(II)

(III)

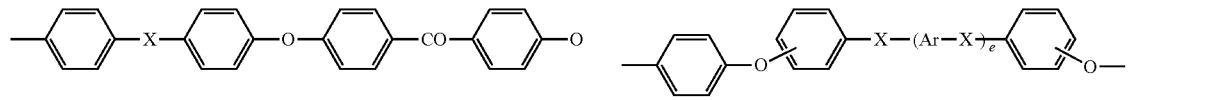

(IV)

-continued
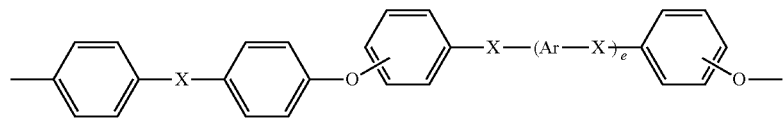
(V)
wherein:
Ar is independently a divalent aromatic radical selected from phenylene, biphenylene or naphthylene,
X is independently O, C(=O) or a direct bond,
n is an integer of from 0 to 3,
b, c, d and e are 0 or 1,
a is an integer of 1 to 4, and
preferably, d is 0 when b is 1.
More preferably, recurring units (R1) are chosen from:
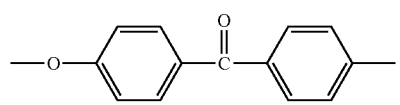
(VI)
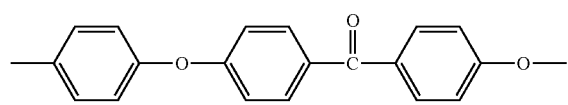
(VII)
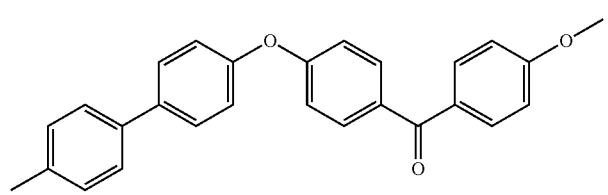
(VIII)
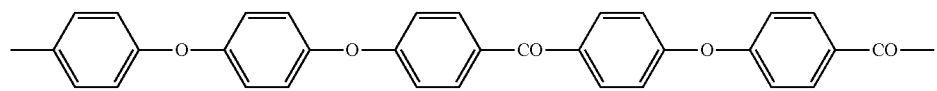
(IX)
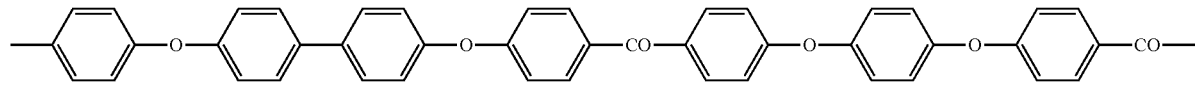
(X)
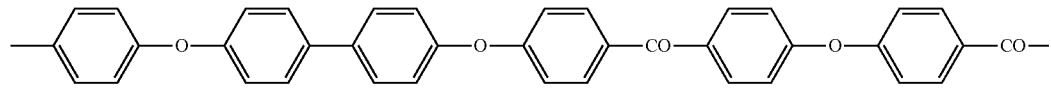
(XI)
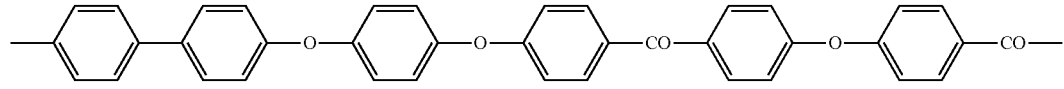
(XII)
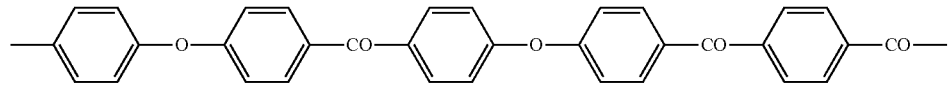
(XIII)
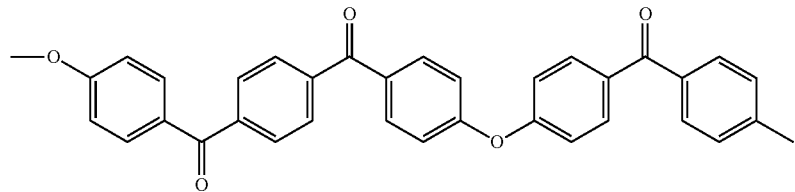
(XIV)

-continued (XV)
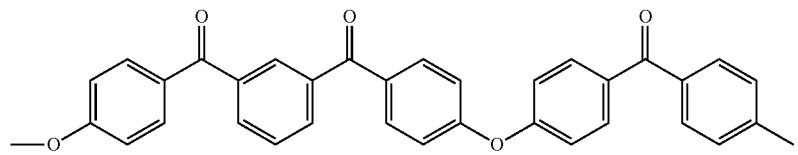

Still more preferably, recurring (R1) are chosen from:

(VI)
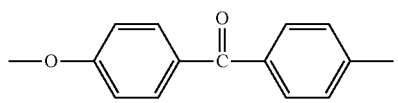

(VII)
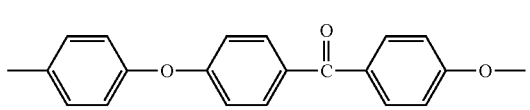
and (VIII)
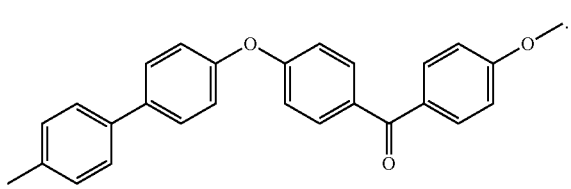

Most preferably, recurring units (R1) are:

(VII)
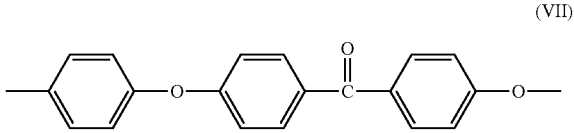

(VI)
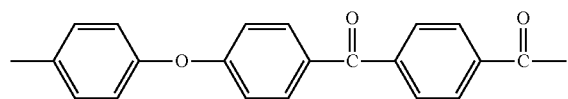

A PEEK polymer is intended to denote any polymer of which more than 50 wt. % of the recurring units are recurring units (R1) of formula (VII). A PEK polymer is intended to denote any polymer of which more than 50 wt. % A) of the recurring units are recurring units (R1) of formula (VI).

The poly(aryl ether ketone) may be notably a homopolymer, a random, alternate or block copolymer. When the poly(aryl ether ketone) is a copolymer, it may notably contain (i) recurring units (R1) of at least two different formulae chosen from formulae (VI) to (XV), or (ii) recurring units (R1) of one or more formulae (XVI) to (XXV) and recurring units (R1*) different from recurring units (R1):

(XVI)
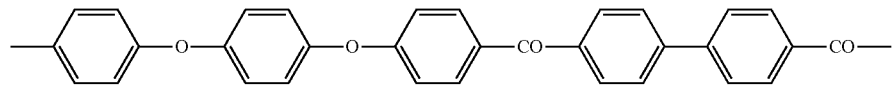

(XVII)

(XVIII)

(XIX)
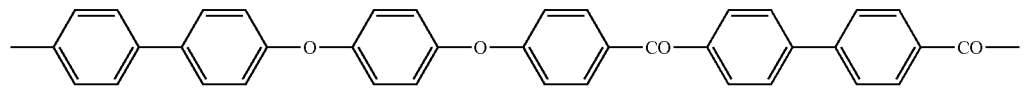

(XX)
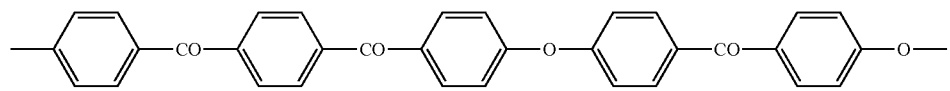

(XXI)
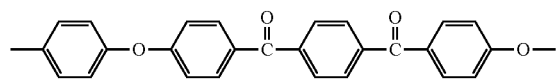

(XXII)
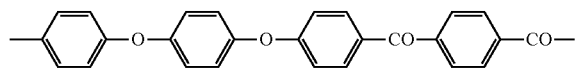

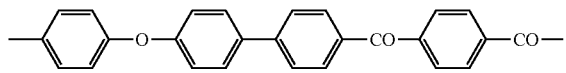
(XXIII)

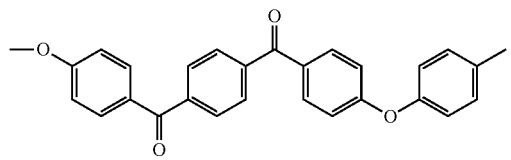
(XXIV)

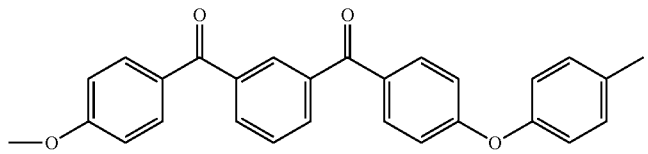
(XXV)

Preferably more than 70 wt. %, more preferably more than 85 wt. % of the recurring units of the poly(aryl ether ketone) are recurring units (R1). Still more preferably, essentially all the recurring units of the poly(aryl ether ketone) are recurring units (R1). Most preferably, all the recurring units of the poly(aryl ether ketone) are recurring units (R1).

The PAEK according to the present invention is a semi-crystalline PAEK, preferably a semi-crystalline PEEK. A semi-crystalline PAEK is intended to denote a PAEK featuring areas of crystalline molecular structure, but also having amorphous regions. In contrast with completely amorphous PAEKs, semi-crystalline PAEKs have generally a melting point. Very often, the existence of a melting point is detected and the value of the melting point is measured by Differential Scanning calorimetry, for example as reported in the examples. The melting point is advantageously determined by a certain construction procedure on the heat flow curve: the intersection of the two lines that are tangent to the peak at the points of inflection on either side of the peak define the peak temperature, namely the melting point. In accordance with the present invention, the semi-crystalline PAEK has a melting point advantageously greater than 150° C., preferably greater than 250° C., more preferably greater than 300° C. and still more preferably greater than 325° C.

A particularly preferred PAEK polymer prepared using the invention 4,4'-DFBP is a homopolymer of recurring units (R1) of formula (VII), i.e. a polymer of which all the recurring units of the poly(aryl ether ketone) are recurring units (R1) of formula (VII).

This PEEK homopolymer preferably has a RV of between 0.50 and 1.40; more preferably between 0.60 and 1.30 and can be made using, e.g., the invention 4,4'-DFBP and p-hydroquinone. Using the DSC conditions detailed in the examples, the target heat of fusion in Jig for this PEEK polymer is preferably ≥68.0-26.6*RV (dl/g) where RV is the polymer reduced viscosity measured at 25° C. in concentrated $H_2SO_4$, as detailed in the examples.

U.S. Pat. Nos. 3,953,400, 3,956,240, 3,928,295, and 4,176,222, and RE 34085, all incorporated herein by reference, also disclose PAEK resins and methods for their preparation. As noted above, PAEK polymers are generally prepared by aromatic nucleophilic substitution. For example, a bisphenol can be deprotonated with a base such as NaOH, $Na_2CO_3$ or $K_2CO_3$ and the resultant bisphenolate may then react with, e.g., a dihalobenzophenone, especially 4,4'-DFBP, via nucleophilic substitution with the halogen atoms of the dihalobenzophenone, especially the fluorine atoms of the 4,4'-difluorobenzophenone (4,4'-DFBP), acting as leaving groups.

Such PAEK reactions are typically carried out in a solvent, that often is, or that often contains, diphenylsulfone. However, other solvents can be used: benzophenone, dibenzothiophene dioxide, etc.

In the process according to the present invention, a semi-crystalline PAEK is prepared by reacting a nucleophile with a 4,4'-DFBP meeting the specific one or more impurity limitation(s) as previously detailed.

In the process according to the present invention, various nucleophiles may be used. The nucleophile used in the present invention is preferably selected from the group consisting of p-hydroquinone (commonly known as "hydroquinone"), 4,4'-dihydroxybenzophenone, 4,4'-biphenol, 1,4-bis-(p-hydroxybenzoyl)benzene, 1,3-bis-(p-hydroxybenzoyl)benzene and mixtures thereof. More preferably, it is p-hydroquinone. In the process according to the present invention, the reacting of the nucleophile with the 4,4'-difluorobenzophenone takes advantageously place via aromatic nucleophilic substitution in a solvent. The solvent includes preferably diphenylsulfone meeting one or more impurity limitations, as specified in embodiment (D) hereinafter.

Embodiment (D)

In a preferred embodiment (D) of the present invention, the process for preparing a semi-crystalline poly(aryl ether ketone) is a process by reacting a nucleophile with a 4,4'-difluorobenzophenone via aromatic nucleophilic substitution in a solvent comprising a diphenylsulfone, wherein said diphenylsulfone meets at least one of the following impurity limitations:

| | |
|---|---|
| Monomethyldiphenylsulfone content (sum of all isomers) | Less than 0.2 area % |
| Monochlorodiphenylsulfone content (sum of all isomers) | Less than 0.08 area % |
| Sodium content | Less than 55 ppm |
| Potassium content | Less than 15 ppm |
| Iron content | Less than 5 ppm |
| Residual acidity content | Less than 2.0 µeq/g |
| Diphenylsulfide content | Less than 2.0 wt. % |
| APHA of 20 wt. % solution in acetone at 25° C. | Less than 50 |
| Total chlorine content | Less than 120 ppm | where ppm and wt. % are based on the total weight of the diphenylsulfone and area % represents the ratio of the GC peak area of the impurity of concern over the total area of all GC peaks of the diphenylsulfone.

The residual acidity content in diphenylsulfone can be determined as follows. Approximately 3 g of diphenylsulfone sample is weighed to the nearest 0.1 mg and added to an empty glass titration vessel. 55 ml of high-purity methylene chloride is added, followed by addition of a 5.00 ml aliquot of spiking solution, which contains six drops of 37% hydrochloric acid per liter, into the same titration vessel. The vessel is then attached to the titrator cell assembly containing the buret tip, pH electrode, and magnetic stirrer. The vessel is then purged with carbon dioxide free nitrogen for 5-7 minutes. While continuing the nitrogen purge, the vessel contents is titrated with 0.025 N tetrabutylammonium hydroxide in 1:12 methanol:toluene and the volume of titrant required to reach the strong acid endpoint is measured. A blank titration is performed using the same parameters, except that the sample was omitted. Results are calculated using the following equation:

$$\text{Acidity} = ((VS1\,VB1)*N*100000)/W \text{ in microequivalents per gram of sample}$$

Where VS1 is the amount of titrant in ml required to reach the strong acid/base equivalence points when sample solution is titrated and VB1 is the amount of titrant in ml required to reach the strong acid/base equivalence point when only the blank solution is titrated, W is the sample weight, and N is the normality of the tetrabutylammonium hydroxide titrant. If acidity is negative, the sample contains basic species.

The sodium, potassium, and iron content in diphenylsulfone can be determined as follows. Concentrations of sodium, potassium, and iron are measured in diphenylsulfone by ashing of the sample followed by measurement of element concentration by inductively-coupled plasma atomic emission spectrometry. Approximately 3 g of diphenylsulfone sample is weighed into platinum crucibles using an analytical balance. Two drops of concentrated, trace metals grade sulfuric acid is added to each sample and the crucibles are placed into a muffle furnace set to 250° C. After the diphenylsulfone has vaporized, the furnace temperature is raised to 525° C. for 1 hour to remove any organic residues. Metallic residues are dissolved by adding 1 ml of concentrated hydrochloric acid to the crucible and warming at 50° C. to dissolve the ash. After addition of 5 ml of deionized water and additional warming, crucible contents are quantitatively transferred to a 25-ml volumetric flask, diluted to the mark with deionized water, and mixed well. The diluted solutions are then analyzed by ICP-AES against standards made from certified sodium, potassium, and iron standard solutions. Emission is monitored at the following wavelengths for the elements of interest: sodium:589.592 nm, potassium:766.490 nm and iron:238.204 nm. Plasma conditions used for the analysis are: plasma input power: 1300 watts, plasma argon flow:15 liters per minute, auxiliary argon flow:0.5 liters per minute, nebulizer flow:1.2 liters per minute, and sample flow rate:1.5 milliliters per minute. Element concentrations in the samples are calculated by the ICP operating software from the element emission line intensities.

The total chlorine content in diphenylsulfone can be determined as follows. Using forceps, a clean, dry combustion boat is placed onto a microbalance, and the balance is zeroed. 1 mg of diphenylsulfone sample is weighed into the boat and weight is recorded to 0.001 mg. The combustion boat and sample are placed in the introduction port of a Thermo Electron Corporation ECS 1200 Halogen Analyzer, and the port is capped. The sample weight is entered into the sample weight field on the instrument computer. The sample analysis cycle is then started. The sample is burned in a mixture of argon and oxygen and the combustion products are carried by the combustion gas stream into a titration cell. Hydrogen chloride produced from the combustion is absorbed into the cell solution from the gas stream, and is coulometrically titrated with silver ions. Total chlorine content is displayed at the end of the titration.

The diphenylsulfide content in diphenylsulfone can be determined by liquid chromatography, as explained hereinafter. HPLC analysis is carried out on a Waters Alliance 2795 LC instrument using a Supelco Discovery HS F5 25 cm×4.6 mm column. The analysis conditions are:

Mobile phase: acetonitrile/deionized water.
Gradient: 60/40 acetonitrile/water, hold for 5 minutes, increase to 100% acetonitrile in further 10 minutes, hold for 5 minutes at 100% acetonitrile
Flow rate: 1 ml/minute
Injection volume: 10 µl
Detection: UV at 254 nm The sample is prepared by dissolving 0.2 g of DPS in 10 g of acetonitrile. The concentration of diphenylsulfide is determined using a low concentration diphenylsulfide as an external calibration standard (commercially available). The retention time for DPS is typically 6.2 minutes and the retention time for diphenylsulfide is typically 10.7 minutes. The diphenylsulfide concentration in the DPS sample is assessed by the area of the diphenylsulfide peak/total peak area of DPS plus impurities.

The monochlorodiphenylsulfone and monomethyldiphenylsulfone content in diphenylsulfone can be determined by gas chromatography, as explained hereinafter. GC analysis is performed on an HP5890 series 11 gas chromatograph using a Restek RTx-5MS, 15 m×0.25 mm internal diameter×0.25 µm film thickness column. The following GC conditions are used:

Helium flow rate: 1 ml/minute,
Injector temperature: 250° C.
FID temperature: 250° C.
Oven Temperature Program: 100° C., hold 1 minute, 30° C./minute to 250° C., hold 1 minute
Total run time: 14 minutes
Injection volume: 1 µl
Split 40:1

The sample is prepared by dissolving 0.2 g of DPS in 5 ml of acetone. The GC retention times for monomethyldiphenylsulfone isomers are typically 8.0 and 8.1 minutes and for monochlorodiphenylsulfone 8.2 minutes. The identity of the impurities is determined by GCMS run on the sample solution. The impurity concentrations are quoted as area %, calculated from GC FID peak areas. When several isomers are present, the concentration includes the sum of these isomers.

The color (APHA) of DPS in acetone can be determined as follows. 20 g of diphenylsulfone are dissolved in 80 g of acetone at 25° C. The acetone used contains less than 0.5 wt. % water. Color of the solution is measured as compared to Pt—Co standards in the APHA scale (ASTM D1209-00), using a Gretag Macbeth Color Eye Ci5 Spectrophotometer for the comparison. The blank used is distilled water.

In the process in accordance with embodiment (D) of the present invention, said diphenylsulfone meets preferably the impurity limitations for monomethyldiphenylsulfone, monochlorodiphenylsulfone, and residual acidity.

Additionally or alternatively, in the process in accordance with embodiment (D) of the present invention, said diphenylsulfone meets preferably the impurity limitations for sodium, iron, diphenylsulfide, and APHA of 20 wt. % solution in acetone at 25° C.

In the process in accordance with embodiment (D) of the present invention, excellent results were obtained when all the impurity limitations as above recited were met.

In the process according to the present invention, the reacting of the nucleophile with the 4,4'-difluorobenzophenone takes advantageously place via aromatic nucleophilic substitution in the presence of alkali-metal carbonate, often under an inert atmosphere and often at temperatures approaching the melting point of the polymer. The alkali-metal carbonate includes preferably particulate sodium carbonate having a certain particle size distribution, as specified in embodiment (E) hereinafter.

Embodiment (E)

In a preferred embodiment (E) of the present invention, the process for preparing a semi-crystalline poly(aryl ether ketone) is a process by reacting a nucleophile with a 4,4'-difluorobenzophenone via aromatic nucleophilic substitution in the presence of particulate sodium carbonate, wherein the 4,4'-difluorobenzophenone meets the one or more impurity limitation(s) as above detailed, and said particulate sodium carbonate has a particle size distribution as follows:

$D_{90} \geq 45$ μm and $D_{90} \leq 250$ μm and $D_{99.5} \leq 710$ μm.

As used herein, a sodium carbonate particle size distribution expressed as $D_{xx} \leq Y$ μm refers to the percentage (xx %) of sodium carbonate particles by weight in a sample that are less than or equal to Y μm in diameter.

On one hand, in accordance with embodiment (E), $Na_2CO_3$ that is "too fine" is avoided as it can notably lead to a low bulk density product that is difficult to handle and synthesis reaction kinetics that are difficult to control. With this regard, the Applicant found that $Na_2CO_3$ with a $D_{90} \geq 45$ μm was beneficial.

On the other hand, in accordance with embodiment (E), $Na_2CO_3$ that contains a certain amount of "big" particles, and especially of "very big" particles (i.e., typically of about 710 μm or more), is also to be avoided as it can notably slow down the polymerization rate, or require the use of an undesirably high amount of $K_2CO_3$ or other higher alkali metal carbonate (at fixed $Na_2CO_3$ amount); $Na_2CO_3$ that contains a certain amount of "big" particles, and especially of "very big" particles, can also result in polymerizations having poor kinetics consistency. With this regard, the Applicant found that $Na_2CO_3$ with a $D_{90} \leq 250$ μm and with a $D_{99.5} \leq 710$ μm was also beneficial.

The use of particulate sodium carbonate in accordance with embodiment (E) provides several benefits, including the ability to synthesize easily PAEKs in the absence of a cosolvent forming an azeotrope with water such as p-xylene, and thereby prepare PAEKs with no trace of residual cosolvent (such cosolvents, like p-xylene, are generally toxic). Cosolvents forming an azeotrope with water used in the synthesis of PAEK resins are known to those of skill in the art, and in addition to p-xylene include chlorobenzene, toluene, etc. The use of particulate sodium carbonate in accordance with embodiment (E) makes it also possible to manufacture lower color, whiter PAEK resins. The use of particulate sodium carbonate in accordance with embodiment (E) results also beneficially in improved kinetics consistency.

Preferably, the $D_{99.5}$ of the sodium carbonate particles in accordance with embodiment (E) is of at most 630 μm; more preferably, it is of at most 500 μm; still more preferably, it is of at most 425 μm; most preferably, it is of at most 355 μm.

Preferably, the $D_{90}$ of the sodium carbonate particles in accordance with embodiment (E) is of at least 63 μm; more preferably, it is of at least 90 μm; still more preferably, it is of at least 112 μm.

Preferably, the $D_{90}$ of the sodium carbonate particles in accordance with embodiment (E) is of at most 212 μm; more preferably, it is of at most 180 μm; still more preferably, it is of at most 150 μm.

In certain preferred sub-embodiments of embodiment (E), the sodium carbonate has the following particle size distributions:

$D_{99.5} \leq 630$ μm, $D_{90} \leq 212$ μm, and $D_{90} \geq 45$ μm; or
$D_{99.5} \leq 500$ μm, $D_{90} \leq 212$ μm, and $D_{90} \geq 45$ μm; or
$D_{99.5} \leq 425$ μm, $D_{90} \leq 212$ μm, and $D_{90} \geq 45$ μm; or
$D_{99.5} \leq 630$ μm, $D_{90} \leq 180$ μm, and $D_{90} \geq 45$ μm; or
$D_{99.5} \leq 500$ μm, $D_{90} \leq 180$ μm, and $D_{90} \geq 45$ μm; or
$D_{99.5} \leq 425$ μm, $D_{90} \leq 180$ μm, and $D_{90} \geq 45$ μm; or
$D_{99.5} \leq 630$ μm, $D_{90} \leq 212$ μm, and $D_{90} \geq 63$ μm; or
$D_{99.5} \leq 500$ μm, $D_{90} \leq 212$ μm, and $D_{90} \geq 63$ μm; or
$D_{99.5} \leq 425$ μm, $D_{90} \leq 212$ μm, and $D_{90} \geq 63$ μm; or
$D_{99.5} \leq 630$ μm, $D_{90} \leq 212$ μm, and $D_{90} \geq 90$ μm; or
$D_{99.5} \leq 500$ μm, $D_{90} \leq 212$ μm, and $D_{90} \geq 90$ μm; or
$D_{99.5} \leq 425$ μm, $D_{90} \leq 212$ μm, and $D_{90} \geq 90$ μm.

The particle size distribution of the sodium carbonate in accordance with embodiment (E) can be determined by mechanical sieving. This method is appreciated because of its easiness, broad availability, and excellent repeatability. Mechanical sieving is generally based on the mechanical separation of the various fractions on a series of superimposed sieves. The analysis can be made partly or fully in accordance with ASTM E 359-00 (reapproved 2005)[e1], the whole content of which being herein incorporated by reference. ASTM E 359-00 (reapproved 2005)[e1] concerns various measurements made specifically on sodium carbonate, notably sieve analysis. The particle size distribution is advantageously determined with an automatic mechanical sieving device, such Ro-Tap RX-29 sieve shaker (as commercialized by W. S. Tyler Company). The sieves mounted on the sieve shaker are advantageously in conformity with standard ISO 3310-1 or ASTM E-11, preferably with wire stainless steel circular sieves with square meshes, metal mounting with a diameter 200 mm. The device and its sieves are advantageously checked periodically using a reference powder; the control frequency should be desirably be as high as possible for early detection of any deviation, as possibly resulting for damaged meshes. Typically, it is proceeded as follows: the sieves are superimposed and assembled from top to bottom by descending order of opening mesh; a fixed weight amount of the powder to be investigated is weighed with an analytical balance and placed on top of the widest sieve; by vibrating the sieving machine, the powder material is conveyed through the various sieves; the sieving operation is run for a fixed amount of time; the residues on the sieves are weighed with an analytical balance and related mathematically to the initial weight of material. Notably $D_{90}$ and $D_{99.5}$ values can be calculated from the residues weights. This calculation is generally made as follows:

1) Calculate the weight percentage of the test specimen retained on each sieve.
2) Express the weight percentage passing through each sieve, and cumulated.

The results can be displayed on a graph were the Y-coordinate represents the cumulative weight percent particles retained on a particular sieve. The X-coordinate corresponds to sieve size. The Y-value for a particular sieve can be determined by adding the weight of the particles retained on that sieve plus the weights of the particles retained on all larger sieves above it and dividing the sum by the total weight of the sample.

The sieves can be ISO 3310-1 or ASTM E-11 test sieves having a diameter of 200 mm, notably commercialized from LAVAL LAB Inc. A certain suitable set of sieves is composed of eight ISO 3310-1 or ASTM E-11 test sieves having a diameter of 200 mm, having the following aperture size or ASTM opening designation: 1000 μm (ASTM No. 18), 500 μm (ASTM No. 35), 250 μm (ASTM No. 60), 180 μm (ASTM No. 80), 125 μm (ASTM No. 120), 90 μm (ASTM No. 170), 63 μm (ASTM No. 230) and 45 μm (ASTM No. 325).

At the end of the sieving analysis, the weight fraction caught on each screen can be calculated. $\Phi_{i*}$, the fraction on sieve i, of size $x_i$, is thus:

$$\phi_i = \frac{w_i}{\sum_{i=1}^{n} w_i}$$

wherein $w_i$ is the weight of powder collected on sieve i sample weight

The percentage under the size $x_t$, $P_t$ is thus defined as:

$$P_t = \sum_{i=1}^{t-1} \phi_i$$

To obtain the cumulative curve, $P_t$, the percentage under the size $x_t$ can be plotted versus $x_t$. The curve can be built by considering in each point the following slope:

$$\left(\frac{dP}{dx}\right)_{x=x_t} = \frac{\phi_t}{x_{t+1} - x_t}$$

3) Determine $D_z$ values (0<z<100), e.g. determine $D_{90}$ and $D_{99.5}$.

$D_z$ is defined as the abscissa of the curve for P=z/100, i.e. z wt. % of the sample is under the size of $D_z$.

$D_{90}$ is defined as the abscissa of the curve for P=0.90, i.e. 90 wt. % of the sample is under the size of $D_{90}$.

$D_{99.5}$ is defined as the abscissa of the curve for P=0.995, i.e. 99.5 wt. % of the sample is under the size of $D_{99.5}$.

Exemplary Method for Measuring the Particule Size Distribution, in Particular the $D_{90}$ and $D_{99.5}$, of Particulate $Na_2CO_3$ Apparatus:
Mechanical sieving apparatus able to transmit combined movements in the horizontal plane and shocks along the vertical axis to a pile of superimposed sieves (apparatus used: RO-TAP RX-29 Model or equivalent, with 278 horizontal revolutions and 150 taps per minute)
Series of circular sieves, wire stainless steel with square meshes, metal mounting with a diameter 200 mm, in conformity with NF ISO 3310-1 standard and periodically checked using a reference powder.
Sieves superimposed by descending order of opening mesh (size in μm): 1000 μm, 500 μm, 250 μm, 180 μm, 125 μm, 90 μm, 63 μm and 45 μm.

Analytical balance, accuracy 0.01 g.
Method:
Test Specimen: 70 g of powder weighed to 0.01 g.
Transfer the test specimen on the pile of sieves and position it in the apparatus
Sieve for 15 minutes.
Weigh the content of each sieve to 0.01 g.
Calculation:
Calculate the weight percentage of the test specimen retained on each sieve.
Express the weight percentage passing through each sieve, and cumulated.
Determine by graphical interpolation the mesh opening equivalent to the 90% and 99.5% cumulated weight percentage ($D_{90}$, $D_{99.5}$).

The particle size distribution of the sodium carbonate used in accordance with embodiment (E) is advantageously determined on a sample which is representative of the whole sodium carbonate which is used in said process. To achieve appropriate sampling, the skilled person will advantageously rely upon all those sampling recommendations which do form part of the general knowledge and are broadly described in various encyclopaedias, including but not limited to "Sampling", Reg. Davies, in "Kirk-Othmer Encyclopaedia of Chemical Technology", online Ed. 2000, the whole content of which is herein is incorporated by reference. Since sodium carbonate can be viewed as a free-flowing powder, sampling procedures suitable for stored free-flowing powders will be used preferably.

Sodium carbonate is broadly commercially available, either in the form of dense sodium carbonate or light sodium carbonate. Light sodium carbonate, also called light soda ash, has generally a free flowing density, as measured in accordance with ISO 903 standard, of between 0.48 kg/dm³ and 0.65 kg/dm³. Dense sodium carbonate, commonly called dense soda ash, has generally a free flowing density, as measured in accordance with ISO 903 standard, of from 0.90 kg/dm³ to 1.20 kg/dm³. In general, neither the commercially available dense sodium carbonates nor the commercially available light sodium carbonates have a particle size distribution as required by embodiment (E). Yet, as will explained below, it is easy for the skilled person, searching for obtaining a sodium carbonate with the appropriate particle size requirements, to obtain it.

Dense sodium carbonates having the particle size distribution as required by present embodiment (E) can be notably obtained by appropriate grinding and/or sieving dense sodium carbonates having a particle size distribution not in accordance with embodiment (E). Insofar as dense sodium carbonates are concerned, methods including at least one grinding step followed by at least one sieving step are preferred. As suitable grinders, it can be notably cited jet mills such as helical jet mills, oval tube jet mills, counterjet mills, fluidized bed jet mills, and ball and plate jet mills, can notably be used. As suitable sieves, it can be notably cited 710 μm, 630 μm, 500 μm, 400 μm, 300 μm, 250 μm, 200 μm, 150 μm and 125 μm sieves.

Light sodium carbonates having the particle size distribution as required in present embodiment (E) can also be obtained by appropriate grinding and/or sieving light sodium carbonates having a particle size distribution not in accordance with embodiment (E). However, insofar as light sodium carbonates are concerned, methods free of any grinding step are preferred; such methods may include a sieving step or not. A particularly preferred method for obtaining light sodium carbonates having the particle size distribution in accordance with embodiment (E) comprises selecting said light sodium carbonates among different lots of one or more grades of commercially available light sodium carbonates, as detailed below. The Applicant determined the particle size distribution of numerous lots of commercially available (unground) light sodium carbonates from different sources, and observed that, among all these lots, none had a $D_{90}$ below 45 µm; as a matter of fact, their $D_{90}$ often ranged usually from about 100 µm to about 250 µm, i.e. the lots often complied with both requirements set forth for the $D_{90}$ in accordance with embodiment (E) of the present invention. Concerning the $D_{99.5}$ of the commercially available light sodium carbonates, the Applicant observed surprisingly that its variability from one lot to another was very high, including when considering lots produced at relatively short intervals of time by the same manufacturer in the same plant; it deduced wisely therefrom that this variability could be exploited to its own benefit, because, among the lots produced, certain had the appropriate particle size requirements, while certain other lots of the same commercial grade had a $D_{99.5}$ above 710 µm, not in accordance with embodiment (E) of the present invention. Among the tested sodium carbonates, SODAS OLVAY® L sodium carbonate, as produced notably in Dombasle or Rosignano plants, is particularly attractive because a rather high fraction of this commercial grade is formed by lots in accordance with the invention; thus, the Applicant could very easily identify appropriate lots suitable for use in accordance with embodiment (E) of the present invention.

An important and surprising benefit resulting from the use of sodium carbonate powder meeting the requirements of embodiment (E) is that it allows one to limit the amount of potassium carbonate, and more generally of any other higher alkali metal carbonate, to be used in the preparation of the PAEK. As higher alkali metal carbonates other than potassium carbonate, it can be particularly cited rubidium carbonate and caesium carbonate.

Thus, in accordance with embodiment (E), the molar ratio of A/Na (wherein A designates either K, Cs or Rb or any combination thereof) can be of at most 0.050 mol A/mol Na, preferably at most 0.020 mol A/mol Na, and more preferably at most 0.010 mol A/mol Na. In an especially surprising particular sub-embodiment, the molar ratio of A/Na is equal to 0 (i.e. the nucleophilic substitution takes place in the absence of K, Cs and Rb). In another sub-embodiment, the molar ratio of A/Na, although being maintained at a low level (e.g. in accordance with the above specified upper limits), is above 0, preferably of at least 0.001 mol A/mol Na, more preferably of at least 0.002 mol A/mol Na and still more preferably of at least 0.003 mol A/mol Na. Unlike the particle size distribution of the sodium carbonate, the particle size distribution of the potassium carbonate, when present, is not important, although a slight additional improvement in terms of polymerization kinetics might be observed when using a very finely ground potassium carbonate.

In a particular sub-embodiment of embodiment (E), the method for the preparation of a poly(aryletherketone) meets further the technical limitations as met in accordance with previously described embodiment (D).

EXAMPLES

Analytical Methods

DSC Conditions

DSC measurements were done according to ASTM D3418-03, E1356-03, E793-06, E794-06 on TA Instruments DSC 2920 with nitrogen as carrier gas (99.998% purity, 50 ml/min). Temperature and heat flow calibrations were done using indium. Sample size was 5 to 7 mg. The weight was recorded 10.01 mg.

The heat cycles were:
1st heat cycle: 50.00° C. to 380.00° C. at 20.00° C./min, isothermal at 380.00° C. for 1 min.
$1^{st}$ cool cycle: 380.00° C. to 50.00° C. at 20.00° C./min, isothermal for 1 min.
$2^{nd}$ heat cycle: 50.00° C. to 380.00° C. at 20.00° C./min, isothermal at 380.00° C. for 1 min.

The enthalpy of fusion was determined on the 2nd heat scan. The melting of PEEK was taken as the area over a linear baseline drawn from 220° C. to a temperature above the last endotherm (typically 370-380° C.).

Melt Flow Index Measurement Conditions

Melt flow index was measured according to ASTM D1238-04 at 400° C. with 2.16 kg load. The die had the following dimensions: 2.0955 mm diameter and 8.000 mm length. A charge of 3 g of dry polymer (dried at 170° C. for 4 hours) was used. $MF_{10}$ is the melt flow index measured after the polymer has been kept 10 minutes in the barrel. $MF_{30}$ is the melt flow index measured under the same conditions but after the polymer has been kept in the barrel at 400° C. for 30 minutes. MFR (melt flow ratio) is the ratio of $MF_{30}/MF_{10}$ and reflects the melt stability of the polymer. MFR<1 indicates an increase of viscosity overtime.

RV Measurement Conditions

Reduced Viscosity (RV) was measured according ASTM D2857-95 (2007) at 25° C. in concentrated sulfuric acid (1 wt. %/vol). The viscometer tube was number 50 Cannon Fenske. The solution used was prepared by dissolving 1.0000±0.0004 g of resin in 100 ml±0.3 ml concentrated sulfuric acid (95-98%, density=1.84). The concentration C in g/dl is equal to the polymer weight in g divided by the volume in dl (100 ml=1 dl). In order to facilitate the dissolution, ground powder (approx mean particle size 200-600 µm) was used. The sample was dissolved at room temperature (no heating).

The solution was filtered on glass frit (medium porosity) before use. The RV was calculated as $$RV = \frac{t_{soln} - t_{solvent}}{t_{solvent} * C}$$

wherein $t_{soln}$ and $t_{solvent}$ are the efflux times measured for the solution and the blank solvent, respectively. The average of at least 3 measurements was used for efflux times. Under these conditions, the efflux times should be longer than 200 s and, no correction for kinetic energy was applied.

Since sulfonation of the polymer can occur in concentrated sulfuric acid, the efflux time of the solution has to be measured within the 3 hours after the preparation of the solution.

Determination of 2,4'-DFBP and 4-Monofluorobenzophenone in 4,4'-Difluorobenzophenone by Liquid Chromatographic Analysis The HPLC method is carried out on a Agilent 1100 LC instrument using a Supelco Discovery HS F5, 5 µm, 25 cm×4.6 mm column. The analysis conditions were:
Mobile Phase: acetonitrile/deionized water
Gradient: 60/40 acetonitrile/water for 5 minutes, increase to 100% acetonitrile in a further 10 minutes.

Flow rate: 1 ml/minute
Detection: UV 254 nm
Temperature: 50° C.
Injection Volume: 5 μl The sample was prepared by dissolving about 0.01 g of 4,4'-DFBP in 100 ml of acetone.

The amount of 2,4'-difluorobenzophenone and 4-monofluorobenzophenone in 4,4'-difluorobenzophenone was determined using a calibration with three external standards of these commercially available compounds, of different concentrations, to generate a calibration curve.

The retention time of 2, 4'-DFBP was about 7.4 minutes and 7.1 minutes for 4-monofluorobenzophenone. The retention time for 4,4'-DFBP was about 7.7 minutes.

Results are expressed as parts per million of the two impurities.

Determination of the Purity of 4,4'-Difluorobenzophenone by Gas Chromatography and of Chlorofluorobenzophenone in 4,4'-Difluorobenzophenone by Gas Chromatography Gas chromatographic analysis was performed on an Agilent HP6890 Gas Chromatograph, using an HP column: HP-5, 15 m×0.25 mm diameter, 0.25 micron film thickness and the running conditions were:
Injector temperature: 290° C.
Detector temperature (FID): 300° C.
Oven ramp: 60° C., hold for 1 minute, then to 325° C. at 30 C/minute, 5 minute hold at 325° C.
Split ratio: 60:1
Injection volume: 0.2 μl
Carrier gas flow (helium): 1 ml/minute The sample is prepared by dissolving 150 mg of 4,4'-difluorobenzophenone in 5 ml of acetone.

The GC retention time for 4,4-difluorobenzophenone is around 5.7 minutes, and about 7.0 minutes for mono-Cl,F-benzophenone.

The 4,4'-DFBP purity is quoted as an area %, calculated from the GC peak areas in the area % table. The chlorofluorobenzophenone impurity peaks were identified by GCMS analysis and their amounts were estimated from their GC peak areas using external standards of commercially available compounds and assuming that isomers had the same response factor.

Determination of Chlorine Content in 4,4'-Difluorobenzophenone

Using forceps, a clean, dry combustion boat was placed onto a microbalance, and the balance was zeroed. 1 mg of 4,4'-difluorobenzophenone sample was weighed into the boat and weight was recorded to 0.001 mg. The combustion boat and sample were placed in the introduction port of a Thermo Electron Corporation ECS 1200 Halogen Analyzer, and the port was capped. The sample weight was entered into the sample weight field on the instrument computer. The sample analysis cycle was then started. The sample was burned in a mixture of argon and oxygen and the combustion products were carried by the combustion gas stream into a titration cell. Hydrogen chloride produced from the combustion was absorbed into the cell solution from the gas stream, and was coulometrically titrated with silver ions. Total chlorine content was displayed at the end of the titration.

The invention will now be illustrated by the following non-limiting examples. In these examples, the amounts are indicated as percentages by weight unless otherwise indicated.

Example 1

In a 500 ml 4-neck reaction flask fitted with a stirrer, a $N_2$ inlet dip tube, a Claisen adapter with a thermocouple plunging in the reaction medium, and a Dean-Stark trap with a condenser and a dry ice trap were introduced 175.00 g of diphenylsulfone [meeting all the impurity limitations of embodiment (D)], 28.00 g of p-hydroquinone, 57.12 g of 4,4'-DFBP containing 780 ppm 4-FBP and less than 40 ppm 2,4'-DFBP as measured by LC (supplied by Jintan Chun-Feng Chemical Co. and used without further purification), 26.77 g of $Na_2CO_3$ (having a $D_{90} \geq 45$ μm, a $D_{90} \leq 250$ μm and a $D_{99.5} \leq 710$ μm) and 1.80 g of very finely ground $K_2CO_3$ ($D_{50} < 45$ μm). The flask content was evacuated under vacuum and then filled with house nitrogen 4 times using a Firestone valve and then placed under a nitrogen purge (30 ml/min). 80.00 g of xylene were then introduced into the reactor and the reaction mixture was heated slowly to 200° C. (1 hour heating period). Xylene/water azeotrope started distilling off at 163-170° C. The reaction mixture was held at 200° C. for 30 minutes and then heated up to 250° C., held at 250° C. for 30 minutes, heated up to 310° C. and held at this temperature for 3 hours. Termination was carried out by adding 1.42 g 4,4'-DFBP (of above-mentioned purity) and 2.21 g LiCl to the reaction mixture and keeping the mixture at 310° C. for an additional 30 minutes. The reactor content was then poured from the reactor into a SS pan and cooled. The solid was broken up and ground through a 2 mm screen. DPS and salts were extracted from the mixture with acetone and water and acidic water (pH=1). The pH of the final wash water was ≥5. The polymer was dried at 120° C. under vacuum. The polymer had a reduced viscosity measured at 25° C. in concentrated $H_2SO_4$ of 1.17. The enthalpy of fusion measured on the $2^{nd}$ heat cycle of the DSC, determined as explained below, was 43.8 J/g.

Examples 2 to 8

Examples 2 to 8 were made using the same procedure as Example 1 but substituting the 4,4'-DFBP used with different 4,4'-DFBP having different levels of 2,4'-DFBP and 4-FBP (supplied by Jintan ChunFeng Chemical Co. or Navin Fluorine and used without further purification). The reaction was stopped at different reaction time to obtain polymer samples with different molecular weights.

Examples 1 through 4 demonstrate that, using 4,4'-DFBP with less than 750 ppm 2,4'-DFBP, polymer with good crystallinity level can be made.

Comparative examples 5 through 8 show that, using 4,4'-DFBP with more than 750 ppm 2,4'-DFBP, polymer with reduced crystallinity level is obtained.

TABLE 1

| Example # | GC purity (area %) | 4FBP (ppm) | 2,4'DFBP (ppm) | RV (dl/g) | ΔH fusion 2nd heat (J/g) | Target ΔH fusion 2nd heat (68.0-26.6*RV) (J/g) |
|---|---|---|---|---|---|---|
| 1 | 99.8 | 780 | <40 | 1.17 | 43.8 | 36.88 |
| 2 | 99.8 | 1089 | <40 | 0.84 | 47.7 | 45.66 |
| 3 | 99.8 | 780 | 307 | 1.13 | 38.8 | 37.94 |
| 4 | 99.8 | 780 | 323 | 0.70 | 51.1 | 49.38 |
| C5 | 99.8 | 1512 | 788 | 0.80 | 44.7 | 46.72 |
| C6 | 99.9 | 780 | 870 | 0.67 | 34.8 | 50.18 |
| C7 | 99.8 | 780 | 1004 | 0.97 | 41.5 | 42.20 |
| C8 | 99.8 | 780 | 1208 | 0.71 | 45.3 | 49.11 |

Surprisingly, the examples 1-4, while featuring a lower GC purity level, gave better results compared to example C6. In other words, impurities different from the 4FBP and 2,4'DFBP (that were specifically detected in these examples)

have minor or no impact at all on the properties of the resulting polymers, and in particular on their enthalpy of fusion.

The enthalpy of fusion from $2^{nd}$ heat cycle in DSC is shown in FIG. 1, which represents the graph of the enthalpy of fusion expressed in J/g versus the reduced viscosity (RV) expressed in dl/g, and where Examples 1-4 are Examples according to the invention, Examples 5-8 are Comparative Examples and the represented line corresponds to the target enthalpy of fusion.

Examples 10 and 11

Examples 10 and 11 were made using the same procedure as in Example 1 but substituting the 4,4'-DFBP used with different 4,4'-DFBP (supplied by Jintan ChunFeng Chemical Co), containing added 2-chloro-4'-fluorobenzophenone (supplied by DSL Chemicals, Shangai) as indicated in Table 2. The melt stability was measured by the ratio of melt flow at 400° C. after 30 minutes over the melt flow measured after 10 minutes. As shown, when the monomer contains more than 5000 ppm of chlorofluorobenzophenone, the polymer exhibits unacceptable melt stability (MFR 0.05). Preferred MFR values include from 0.50 to 1.20.

It is expected that isomers of 2-chloro-4'-fluorobenzophenone would have a similar effect on melt stability.

Example 11 (comparative) shows that high levels of chlorofluorobenzophenone have a deleterious effect on melt stability (MFR too low).

TABLE 2

| Example # | GC purity (area %) | 4FBP (ppm) | 24'DFBP (ppm) | 2-chloro-4'-Fluorobenzophenone (ppm) | [Cl] (wt %) | RV (dL/g) | MF10 (g/10 min) | MFR |
|---|---|---|---|---|---|---|---|---|
| 1 | 99.8 | 780 | <40 | 50 | 0.0008 | 1.17 | 3.28 | 0.66 |
| 2 | 99.9 | 1089 | <40 | 50 | 0.0008 | 0.84 | 23.05 | 1.02 |
| 10 | 99.5 | 780 | <40 | 3450 | 0.052 | 0.93 | 9.47 | 1.02 |
| C11 | 99.2 | 780 | <40 | 6650 | 0.101 | 0.83 | 19.86 | 0.05 |

As described above, the present invention has many facets. In one facet, an advancement is described in that processes for preparing a PAEK polymer by reacting a nucleophile with 4,4'-difluorobenzophenone (4,4'-DFBP) are improved through the use of 4,4'-DFBP that meets one or more of the above purity conditions. In another facet, improved PAEK polymers are produced using the invention 4,4'-DFBP.

Additional aspects and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. Terms such as "contain(s)" and the like as used herein are open terms meaning 'including at least' unless otherwise specifically noted. Phrases such as "mention may be made," etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A process for preparing a semi-crystalline poly(aryl ether ketone), said process comprising reacting a nucleophile with a 4,4'-difluorobenzophenone, wherein the 4,4'-difluorobenzophenone meets the following impurity limitation:

[2,4'-difluorobenzophenone]+[4-monofluorobenzophenone]≤1250 ppm wherein the amounts of 2,4'-difluorobenzophenone and 4-monofluorobenzophenone in 4,4'-difluorobenzophenone are determined by liquid chromatography analysis, and wherein the nucleophile and 4,4'-difluorobenzophenone are reacted in diphenylsulfone solvent that has a total chlorine content of less than 120 ppm.

2. The process according to claim 1, wherein the 4,4'-difluorobenzophenone further meets the following impurity limitation:

[2,4'-difluorobenzophenone]≤750 ppm.

3. The process according to claim 1, wherein the 4,4'-difluorobenzophenone further meets the following impurity limitations:

[2,4'-difluorobenzophenone]≤750 ppm, and
[4-monofluorobenzophenone]≤500 ppm.

4. The process according to claim 1, wherein the 4,4'-difluorobenzophenone further meets the following impurity limitations:

[2,4'-difluorobenzophenone]≤300 ppm, and
[4-monofluorobenzophenone]≤950 ppm.

5. The process according to claim 1, wherein the 4,4'-difluorobenzophenone further meets the following impurity limitations:

[total chlorine content]≤0.075 wt. % wherein the total chlorine content is determined by a combustion followed by microcoulometric titration analysis (TOX).

6. The process according to claim 1, wherein the 4,4'-difluorobenzophenone further meets the following impurity limitations:

[chlorofluorobenzophenone]≤5000 ppm.

7. The process according to claim 1, wherein the 4,4'-difluorobenzophenone has a GC purity of ≤99.9 area %.

8. The process according to claim 7, wherein the 4,4'-difluorobenzophenone has a GC purity of <99.9 area %.

9. The process according to claim 1, wherein the nucleophile is selected from the group consisting of p-hydroquinone, 4,4'-dihydroxybenzophenone, 4,4'-biphenol, 1,4-bis-(p-hydroxybenzoyl)benzene and 1,3-bis-(p-hydroxybenzoyl)benzene.

10. The process according to claim 1, wherein the poly(aryl ether ketone) is poly(ether ether ketone) (PEEK).

11. The process according to claim 10, wherein the poly(aryl ether ketone) has a heat of fusion in J/g≥68.0-26.6*RV (dl/g) where RV is the polymer reduced viscosity measured at 25° C. in concentrated H2SO4.

12. The process according to claim 1, wherein the poly(aryl ether ketone) is poly(ether ketone) (PEK).

13. The process according to claim 1, wherein the nucleophile is reacted with the 4,4'-difluorobenzophenone via aromatic nucleophilic substitution in the presence of particulate sodium carbonate, said particulate sodium carbonate having a particle size distribution as follows:

D90≥45 μm and D90≤250 μm and D99.5≤710 μm.

14. A poly(aryl ether ketone) obtained by or prepared according to the process of claim 1.

* * * * *